(12) United States Patent
Angermund et al.

(10) Patent No.: US 10,261,030 B2
(45) Date of Patent: Apr. 16, 2019

(54) DEVICE AND METHOD FOR TESTING AND INSPECTING INTEGRITY OF A CONTAINER

(71) Applicant: BRISTOL-MYERS SQUIBB COMPANY, Princeton, NJ (US)

(72) Inventors: Steve Angermund, Kinelon, NJ (US); George Currier, North Brunswick, NJ (US); Joe Jy Koo, Weehawken, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 119 days.

(21) Appl. No.: 15/551,359

(22) PCT Filed: Feb. 17, 2016

(86) PCT No.: PCT/US2016/018173
§ 371 (c)(1),
(2) Date: Aug. 16, 2017

(87) PCT Pub. No.: WO2016/137789
PCT Pub. Date: Sep. 1, 2016

(65) Prior Publication Data
US 2018/0045653 A1    Feb. 15, 2018

Related U.S. Application Data

(60) Provisional application No. 62/119,589, filed on Feb. 23, 2015.

(51) Int. Cl.
*B01L 9/06*          (2006.01)
*G01M 3/22*         (2006.01)
(Continued)

(52) U.S. Cl.
CPC ........ *G01N 21/9054* (2013.01); *G01M 3/229* (2013.01); *G01M 3/38* (2013.01);
(Continued)

(58) Field of Classification Search
CPC ........ A61J 1/16; B01L 9/06; B01L 2200/025; B01L 2200/028; G01N 21/8803; G01N 21/9027
See application file for complete search history.

(56) References Cited

U.S. PATENT DOCUMENTS 1,521,648 A * 1/1925 Pickett ................... A47F 5/112
                                                                       211/73
2,206,728 A * 7/1940 Nevins, Jr. .............. A47F 5/112
                                                                       211/73
(Continued)

OTHER PUBLICATIONS

International Search Report and Written Opinion for Int. App. No. PCT/US2016/018173, dated Jun. 17, 2016.

*Primary Examiner* — David A Rogers
(74) *Attorney, Agent, or Firm* — McDonnell Boehnen Hulbert & Berghoff LLP

(57) ABSTRACT

An inspection device and method for testing and inspecting integrity of a container (200) is disclosed. The inspection device has an angled member (102) and a viewing member (104) secured to the angled member. Together, the angled and viewing members are configured to hold a container to be analyzed. The inspection device also includes a cradle (106) secured to the angled member, the cradle including a cavity (108) configured to hold the angled member at an angle. The inspection device also includes a light source holder (110) secured to the viewing member, a leg member (112) extending from the light source holder, and at least one light source (114) extending through the light source holder. The light source has a first end extending outwardly from the light source holder and a second end extending within the light source holder from which light projects. The light from the light source is projected toward the viewing member. The viewing member includes at least one viewing window (105). A lens is located between the second end of the light (Continued)

source and the viewing member, and a filter is located between the lens and the viewing member.

11 Claims, 5 Drawing Sheets

(51) Int. Cl.
    *G01M 3/38*     (2006.01)
    *G01N 21/64*    (2006.01)
    *G01N 21/88*    (2006.01)
    *G01N 21/90*    (2006.01)

(52) U.S. Cl.
    CPC ......... *G01N 21/64* (2013.01); *G01N 21/8803* (2013.01); *G01N 21/9027* (2013.01); *B01L 9/06* (2013.01)

(56) References Cited

U.S. PATENT DOCUMENTS

| | | | | |
|---|---|---|---|---|
| 2,479,743 A | | 8/1949 | Hall et al. | |
| 2,917,183 A | * | 12/1959 | Seelye | B01L 9/06 211/74 |
| 3,199,684 A | * | 8/1965 | Lee | B01L 9/06 108/92 |
| D204,258 S | * | 4/1966 | Barrantes et al. | D24/230 |
| 3,458,967 A | | 8/1969 | Fiche | |
| 3,751,172 A | | 8/1973 | Seitz et al. | |
| 4,273,416 A | * | 6/1981 | Blum | B01L 9/06 211/73 |
| 4,278,176 A | * | 7/1981 | Adams | B01L 9/06 206/443 |
| 4,349,510 A | * | 9/1982 | Kolehmainen | G01N 21/76 250/328 |
| 4,363,551 A | * | 12/1982 | Achter | G01N 21/51 356/338 |
| 4,382,679 A | | 5/1983 | Lee | |
| 4,748,125 A | * | 5/1988 | Pizzolante | B01L 9/06 206/460 |
| 4,947,996 A | * | 8/1990 | Harris | A47F 5/112 211/13.1 |
| 4,962,041 A | * | 10/1990 | Roginski | G01N 35/0099 324/687 |
| 5,632,388 A | * | 5/1997 | Morrison | B01L 9/06 211/170 |
| 6,599,712 B1 | * | 7/2003 | Sakakibara | C12Q 1/008 435/17 |
| 6,646,741 B1 | * | 11/2003 | Hoyte | G01N 21/8803 356/338 |
| 8,789,713 B2 | * | 7/2014 | Koller | A47F 7/0028 206/370 |
| 9,545,634 B2 | * | 1/2017 | Fox | B01L 9/06 |
| 9,907,727 B2 | * | 3/2018 | Sharpe | A61J 1/16 |
| 2005/0095717 A1 | * | 5/2005 | Wollenberg | G01N 33/2888 436/60 |
| 2005/0196323 A1 | * | 9/2005 | Itoh | G01N 35/00732 422/82.05 |

\* cited by examiner

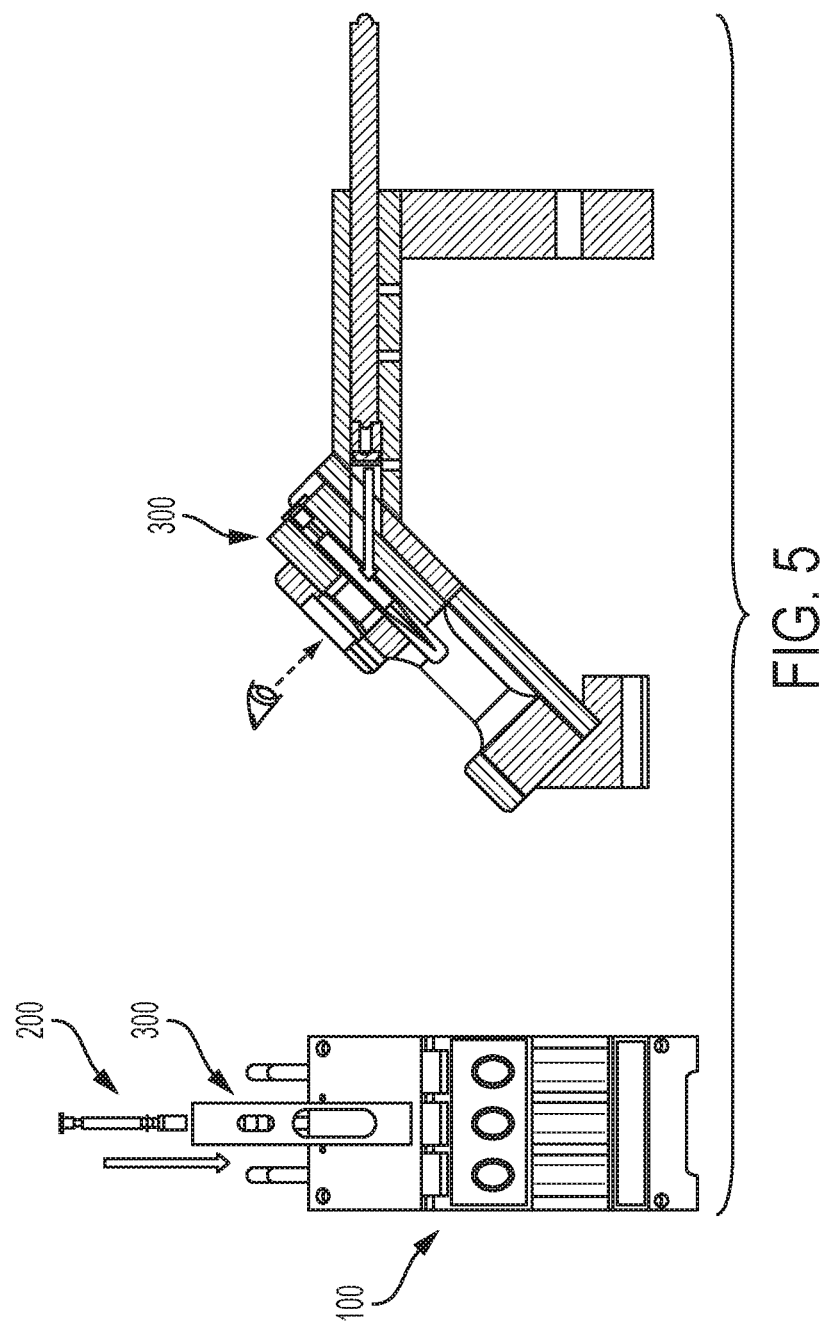

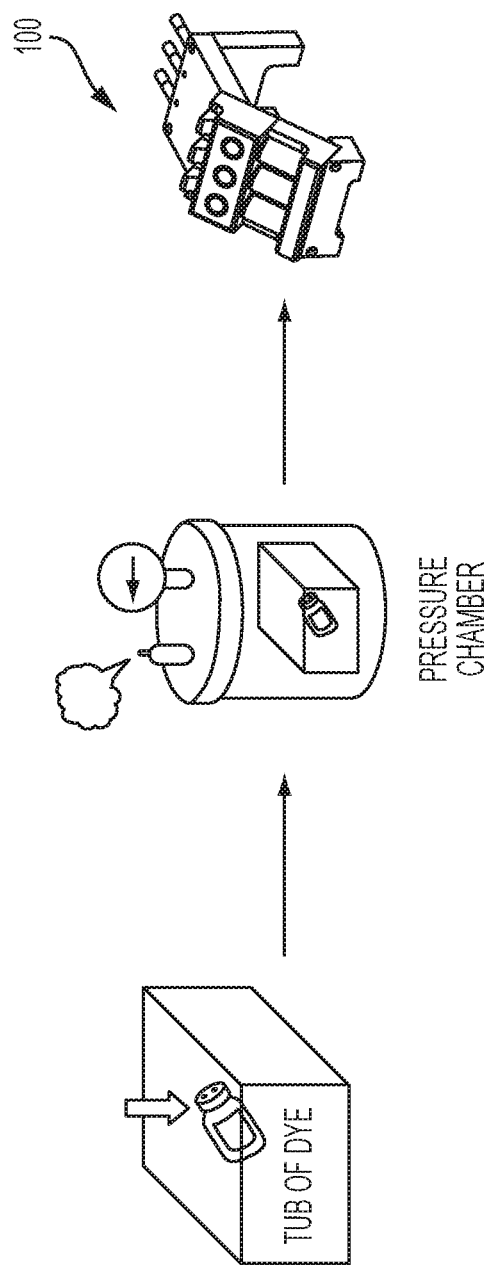

DEVICE AND METHOD FOR TESTING AND INSPECTING INTEGRITY OF A CONTAINER

CROSS-REFERENCE TO RELATED APPLICATION

The present application is a U.S. National Phase Application pursuant to 35 U.S.C. § 371 of International Application No. PCT/US2016/018173 filed Feb. 17, 2016, which claims priority to U.S. Provisional Application No. 62/119,589, filed Feb. 23, 2015. The entire disclosure contents of these applications are herewith incorporated by reference into the present application.

BACKGROUND

A. Field

This disclosure relates generally to container closure integrity testing, and more particularly to a device and method of testing and inspecting the integrity of a container closure.

B. Description of Related Art

Container closure integrity (CCI) of a parenteral pharmaceutical product is defined as the ability of a container closure system to provide protection and maintain quality throughout the shelf life of a sterile drug product. The effectiveness of a container closure system of the primary packaging components (defined as any packaging components that are or may be in direct contact with the dosage form) must be proven to maintain sterility by preventing leakage in or out of the sealed container.

Container closure integrity testing is used to validate the integrity and sterility of a container or container housed within or a part of a delivery system for evaluation of pathogenic ingress. Container closure integrity testing demonstrates the assurance of package integrity concerned with sterile product containment. An effective barrier must be maintained against ingress of microbial organisms, potentially reactive gases (e.g., oxygen), or sometimes loss of vacuum. Examples of type of integrity testing include microbial ingress and dye ingress.

A variety of dyes are suitable for use in the dye ingress test, but the most commonly used is Methylene Blue. The general methodology uses study samples and positive control samples and submerges them into a vat of dye. Positive control samples are typically deliberately breached using capillary tubes of known internal diameter to confirm dye ingress from the test procedure. The vat is placed into a pressure chamber where vacuum and sometimes pressure are applied for a specific amount of time. The samples are removed from the pressure chamber, rinsed, and analyzed by determining whether visible dye is present. A visual test with in situ detection (contents remain in the device) is relatively simple to execute, suitable for use in a quality control environment, and reduces the risk of dye contamination resulting from transfer of the container contents for analysis. Specifics of the methodology used by industry varies greatly between the pressures and time held at those pressures, the sensitivity of the method, the use of positive controls, the breach size used for the controls, and the type of detection used to determine if dye ingressed into the sample.

Currently, a method does not exist for testing of assembled complex drug-filled devices (like an autoinjector) with equivalent sensitivity.

Thus, it would be desirable to provide a method and/or device to improve visual inspection of the sample. It would also be desirable to provide a method for visual inspections to be performed on complex devices (such as an autoinjector) without the need to manipulate the test samples (i.e. cut it open or express the contents).

SUMMARY

The following embodiments and aspects thereof are described and illustrated in conjunction with systems, tools and methods which are meant to be exemplary and illustrative, not limiting in scope.

In one aspect, an inspection device for testing the integrity of a container is described. The inspection device has an angled member and a viewing member secured to the angled member. Together, the angled and viewing members are configured to hold a container to be analyzed. The inspection device also includes a cradle secured to the angled member, the cradle including a cavity configured to hold the angled member at an angle. The inspection device also includes a light source holder secured to the viewing member, a leg member extending from the light source holder, and at least one light source extending through the light source holder. The light source has a first end extending outwardly from the light source holder and a second end extending within the light source holder from which light projects. The light from the light source is projected toward the viewing member. The viewing member includes at least one viewing window. A lens is located between the second end of the light source and the viewing member, and a filter is located between the lens and the viewing member.

In another aspect, a method of testing a container closure for integrity using the inspection device is disclosed. The method includes providing an inspection device having an angled member and a viewing member secured to the angled member. The angled and viewing members are configured to hold a sample container to be analyzed. The inspection device further includes a cradle secured to the angled member, the cradle including a cavity configured to hold the angled member at an angle, a light source holder secured to the viewing member, a leg member extending from the light source holder, and at least one light source extending through the light source holder. The light source has a first end extending outwardly from the light source holder and a second end extending within the light source holder from which light projects. The light from the light source is projected toward the viewing member. The inspection device also includes at least one viewing window located on the viewing member. The method further includes providing a sample container, submerging the sample container in a tub of fluorescein dye, placing dye tub in a chamber for exposure to a pressure-vacuum cycle, rinsing the sample container, placing the sample container in the angled member of the inspection device, and viewing the sample container through the viewing window. When the sample container is viewed through the viewing window, a visual inspection of the sample container in room light without the need for analytical instruments is attainable.

In addition to the exemplary aspects and embodiments described above, further aspects and embodiments will become apparent by reference to the drawings and by study of the following detailed description.

BRIEF DESCRIPTION OF THE DRAWINGS

Exemplary embodiments are illustrated in the drawings. It is intended that the embodiments and figures disclosed herein are to be considered illustrative rather than restrictive.

FIG. 3b is a side view of the portion shown in FIG. 3a;

FIG. 5 shows an alternate embodiment of the device; and

FIG. 6 is an overview of an example method of the present application.

DETAILED DESCRIPTION

An inspection device for use with a container containing a sample, such as an auto-injector, for example, is disclosed. The inspection device is capable of evaluating the container closure integrity of a variety of containers and complex delivery systems without the need for physical manipulation of the containers. The inspection device improves the effectiveness of container closure integrity analysis by enhancing the detectability of the tracking agent. For example, the inspection device allows for visual inspection for container closure integrity without the need for analytical instruments. The inspection device is capable of accommodating various sample presentations, tracking agents, and ambient light conditions. Use of the inspection device alone allows for a qualitative test of container closure integrity. A quantitative analysis is possible when the inspection device is used in combination with an analytical instrument. For example, with the use of a UV-Vis spectrophotometer, the absorbance of the sample can be measured at certain wavelengths to calculate the concentration of dye ingress within the test sample.

Figure 1:
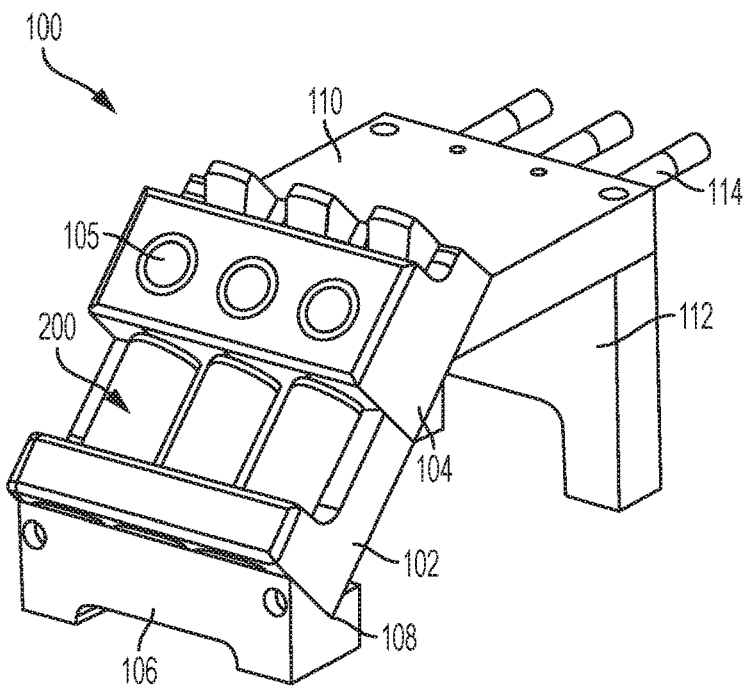
FIG. 1 is a front perspective view of the inspection device of the present application.

FIG. 1 shows an example inspection device 100 for use with a test sample, such as a container 200. In one embodiment, a plurality of containers 200 may be positioned on the inspection device 100 for inspection. Thus, the inspection device 100 can hold three containers 200 simultaneously for analysis. This allows a positive standard (known container with dye) and a negative control (container without dye) to be placed side-by-side with the test container as references (comparative test). The containers 200 and method of analysis are described in more detail below.

The inspection device 100 is composed of modular components to accommodate use of various instruments and test samples with different physical attributes. The inspection device 100 includes an angled member 102. The angled member 102 may be connected to a viewing member 104. Together, the angled and viewing members 102, 104 accommodate one or more containers 200. The angled member 102 may be secured to the viewing member 104 by one or more dowel pins, for example. However, it should be understood that the angled and viewing members 102, 104 may be secured by any known securing means. The viewing member 104 may include one or more viewing windows 105 for viewing the container 200. The viewing window 105 may include an optical filter, lens, or mirrors (not shown) to control the wavelength and/or intensity of the visible luminance from a tracking agent.

Angled member 102 is also secured to a pedestal or cradle member 106. The cradle member 106 may be located at an end of the angled member 102 opposite the viewing member 104. The cradle 106 includes a cavity 108 in which angled member 102 is situated. The cavity 108 is constructed so that the angled member 102, and therefore the container 200, is affixed at an angle with respect to the vertical. The angle will be discussed in more detail below with respect to FIGS. 3a and 3b.

Referring again to FIG. 1, the inspection fixture 100 also includes a light source holder 110 secured to the viewing member 104. The light source holder 110 is positioned substantially horizontal, and at an angle with respect to the viewing member 104. The viewing member 104 may be secured to the light source holder 110 by a fastener such as screws, for example. However, it should be understood that the viewing member 104 and light source holder 110 may be secured by any known securing means.

A leg 112 is secured to the light source holder 110. The leg 112 extends downwardly, and substantially vertically, from the light source holder 110 to stabilize the inspection device.

Figure 2:
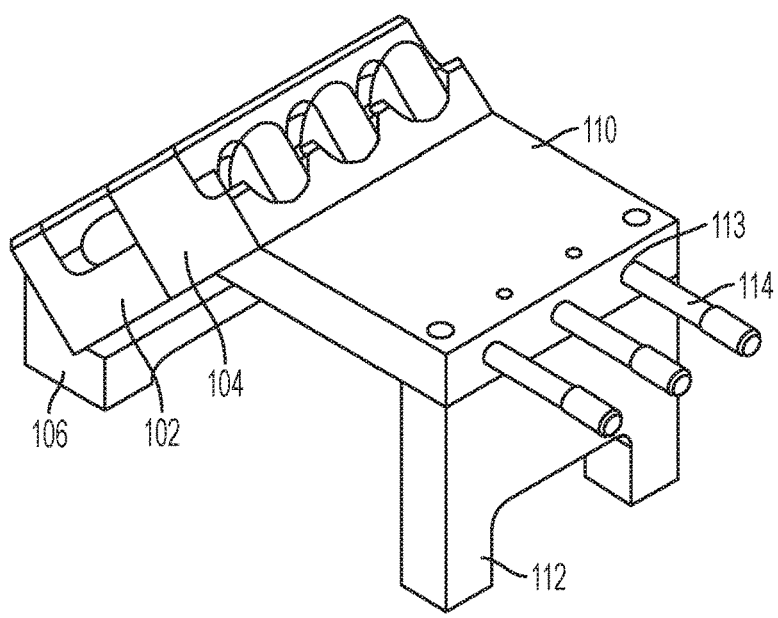
FIG. 2 is a rear perspective view of the device shown in FIG. 1.

As best seen in FIG. 2, one or more light sources 114 are secured to the light source holder 110. In one embodiment, the light source holder 110 includes a plurality of apertures 113 through which the light sources 114 are inserted. The light sources 114 may be secured to the apertures 113 in the light source holder 110 by a fastener such as screws, for example. However, it should be understood that the light sources 114 may be secured to the light source holder 110 by any known securing means. The light sources 114 may each have a first end 115 and a second end 117. The first end 115 extends outwardly from the light source holder 110, and the second end 117 extends within the light source holder. Light projects from the second end 117 toward the viewing member 104, as can be seen by the direction of the arrow shown in FIG. 4.

The light sources 114 may be LEDs, for example. LEDs have a narrow wavelength band to increase absorbance and reduce interference from other wavelengths. In one embodiment, the light from the light sources 114 is blue light. Other types of light may also be used, depending on the application, and on the type of dye used in the test.

Figure 3B:
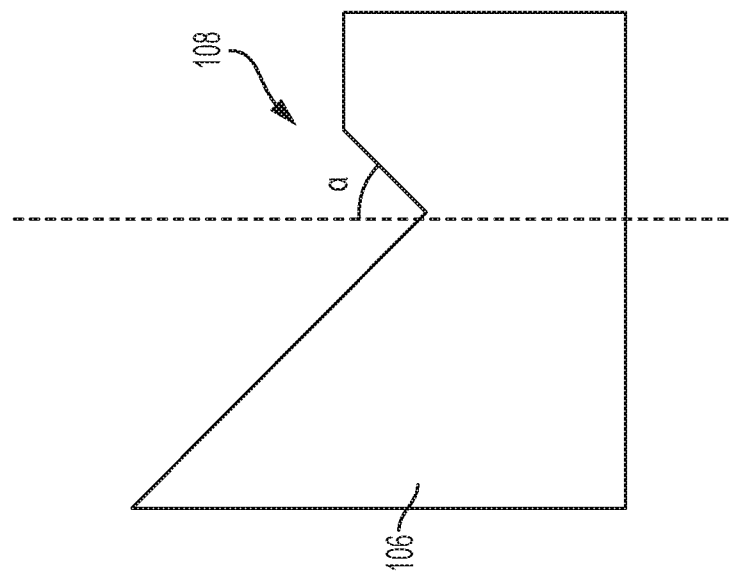
Figure 3A:
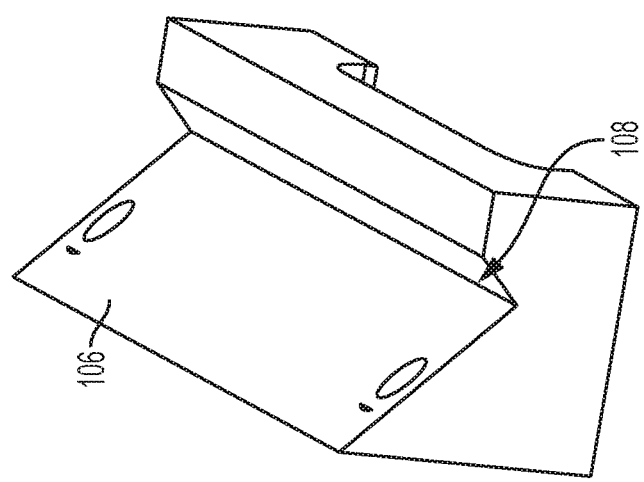
FIG. 3a is close-up view of a portion of the device shown in FIG. 1.

As shown in FIGS. 3a and 3b, the cradle 106 includes a cavity 108. The cavity 108 holds the angled member at an angle α with respect to the vertical. Preferably, the angle α is 45° with the incident light beam so the beam passes through the window in the sample, but is not in line with the line of sight of a viewer. This helps the visibility of dye fluorescence in the container 200 and reduces interference from the light source 114. However, other angles are possible as well depending upon the application and method used.

Figure 4:
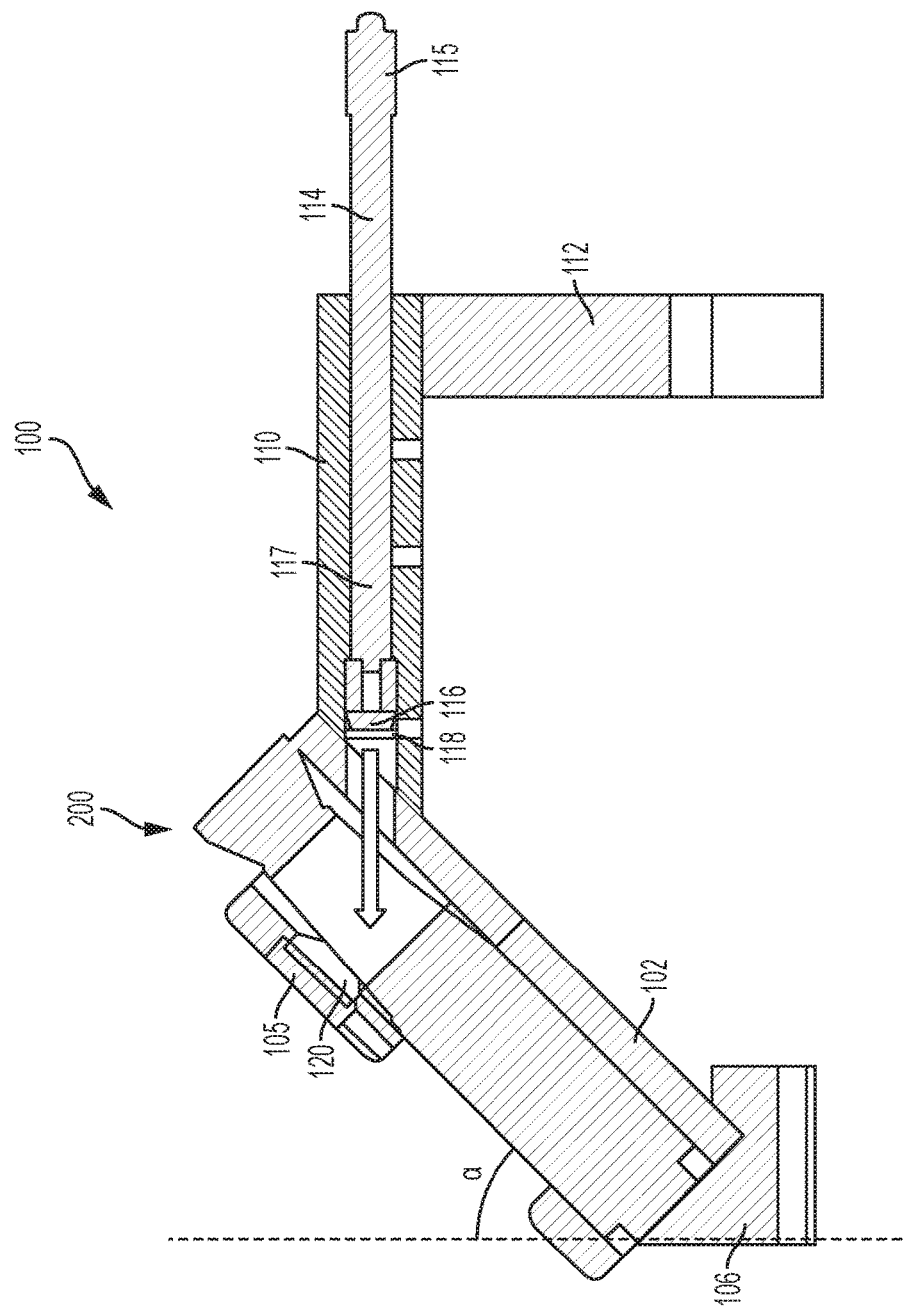
FIG. 4 is a cross-sectional view of the device of FIG. 1.

FIG. 4 is a cross-sectional view of the inspection device 100. A focusing lens 116 and a filter 118 may be positioned at the second end 117 of the light source 114. The focusing lens 116 focuses the light beam onto the area of interest of the container, for example, a window of an auto-injector. The focusing lens 116 reduces interference of light reflecting off of the body of the container. The filter 118 may be a bandpass filter that only allows light at about a 470 nm wavelength (target wavelength from light source) to pass through, but reflects light at other wavelengths in the spectrum. The filter 118 also reduces interference from other wavelengths.

As mentioned above, the viewing windows 105 may also include a filter 120. The filter 120 may be an optical bandpass filter that only allows light at ~515 nm (wavelength of fluorescent glow from dye) to pass, and reflects all other wavelengths. The filter 120 blocks interference from other wavelengths to improve visual sensitivity of dye fluorescence.

As mentioned above, a number of different containers may be analyzed using the inspection device 100. For example, auto-injectors, syringes, vials, bags, medication cassettes, and patch pumps may be analyzed using the inspection device 100. The angled member 102 and viewing member 104 may be modified to accommodate the different containers.

In another embodiment, the angled member 102 and the viewing member 104 can also accommodate the use of an adapter to fit various containers. One example of such an adapter 300 is shown in FIG. 5. The adapter 300 sits at an angle within the angled member 102 and the viewing member 104. A container 200, such as a syringe, can be inserted into the adapter 300 to fit properly in the inspection device 100. The container 200 can then be viewed using the viewing windows 105.

In operation, the inspection device 100 is used in conjunction with a method of testing a container closure for integrity. Referring to FIG. 6, the method includes submerging a container having a test sample, such as container 200, into a tub or vat of dye. In one embodiment, fluorescein dye is used. Fluorescein dye allows a simple visual detection that is sensitive enough to detect small breaches, such as 5 µm, for example). Fluorescent properties of the molecule provide a green glow when exposed to blue light. However, other types of dyes or combinations of dyes and light may be used as well.

The dye should cover the sample completely. The vat is then placed into a pressure chamber where vacuum is applied. In one embodiment, the vacuum reaches a pressure of about 11.8 PSIA, and the vacuum is applied for a minimum of about 30 minutes. The system is then returned to atmospheric pressure for a period of a minimum of about 30 minutes to allow the containers to equilibrate. It should be understood that the specific pressure and time may vary depending upon the type of container and dye used.

Next, pressure is applied for a minimum of about 15 minutes. In one embodiment, the pressure reaches about 29.7 PSIA. The system is then returned to atmospheric pressure for a period of about 30 minutes to allow the containers to equilibrate. Again, it should be understood that the specific pressure and time may vary depending upon the type of container and dye used.

The container 200 is then removed from the pressure chamber, rinsed with clean water, and analyzed. The container 200 may be inspected visually under room light to ensure that the fluorescein dye is rinsed off properly and there are no visual defects in the container.

The container 200 is then placed in the angled portion 102 of the inspection device 100. As mentioned above, a positive and negative control sample is placed on each side of the container 200 as references (comparative test) for fluorescence. A user or viewer then views the container 200 through the viewing window 105. If the sample emits a green glow, then the ingress of fluorescein dye is confirmed, and therefore the container 200 has been breached and is not sterile. If the sample does not emit a green glow, but rather a dark black appearance (or lack of green glow), then the container 200 has not been breached. If the analysis is indeterminate, then a spectrophotometric analysis may be applied.

In one embodiment, the light sources 114 include 470 nm wavelength light, which is optimized to the peak absorbance wavelength of the fluorescein dye tracker used in the test. More light absorbance leads to more fluorescence from the dye.

The inspection device 100 may be constructed of a polymer, such as polyoxymethylene copolymer Delrin, for example. In other embodiments, the inspection device 100 may be constructed of other suitable materials.

The increased test sensitivity of the present application improves detection of potential breaches which enhances product quality and process robustness. The inspection device is versatile and can work with a range of device presentations and will streamline method development, saving time (months) and required test samples (20-315 vials or syringes).

While a number of exemplary aspects and embodiments have been discussed above, those of skill in the art will recognize that still further modifications, permutations, additions and sub-combinations thereof of the features of the disclosed embodiments are still possible. It is therefore intended that the following appended claims and claims hereafter introduced are interpreted to include all such modifications, permutations, additions and sub-combinations as are within their true spirit and scope.

The invention claimed is:

1. An inspection device for testing the integrity of a container, the inspection device comprising:
   an angled member;
   a viewing member secured to the angled member, the angled and viewing members being configured to hold a container to be analyzed;
   a cradle secured to the angled member, the cradle including a cavity configured to hold the angled member at an angle;
   a light source holder secured to the viewing member;
   a leg member extending from the light source holder;
   at least one light source extending through the light source holder, the light source having a first end extending outwardly from the light source holder, and a second end extending within the light source member from which light projects, the light from the light source being projected toward the viewing member;
   at least one viewing window located on the viewing member;
   a lens located between the second end of the light source and the viewing member; and
   a filter located between the lens and the viewing member.

2. The inspection device of claim 1 wherein the light source comprises blue light.

3. The inspection device of claim 1 wherein the angle is 45°.

4. The inspection device of claim 1 wherein viewing window includes an optical filter, a lens, or mirrors.

5. The inspection device of claim 1 wherein the container to be analyzed is an auto-injector.

6. The inspection device of claim 1 further comprising an adapter configured to be attached to the inspection device for accommodating various containers.

7. A method of testing a container closure for integrity using an inspection device, the method comprising:
   providing an inspection device comprising:
      an angled member;
      a viewing member secured to the angled member, the angled and viewing members being configured to hold a container to be analyzed;
      a cradle secured to the angled member, the cradle including a cavity configured to hold the angled member at an angle;
      a light source holder secured to the viewing member;
      a leg member extending from the light source holder;
      at least one light source extending through the light source holder, the light source having a first end extending outwardly from the light source holder, and a second end extending within the light source holder from which light projects, the light from the light source being projected toward the viewing member; and at least one viewing window located on the viewing member;

providing a sample container;

submerging the sample container in a tub of fluorescein dye;

placing dye tub in a chamber for exposure to a pressure-vacuum cycle;

rinsing the sample container;

placing the sample container in the angled member of the inspection device; and viewing the sample container through the viewing window;

wherein when the sample container is viewed through the viewing window, a visual inspection of the sample container without the need for analytical instruments is attainable.

8. The method of claim 7 wherein when the sample container is viewed through the viewing window, a green glow is emitted when dye is present in the sample container and a dark black glow is emitted when dye is not present in the sample container.

9. The method of claim 7 further comprising placing a positive control container and negative control container in the inspection device adjacent to the sample container.

10. The method of claim 7 wherein the light source comprises blue light.

11. The method of claim 7 wherein the sample container is an auto-injector.

* * * * *